(12) United States Patent
Hacker

(10) Patent No.: US 10,835,937 B1
(45) Date of Patent: *Nov. 17, 2020

(54) SURGICAL DRAPE PLUME EVACUATOR

(71) Applicant: Nano 2.0 Business Press, LLC, Delray Beach, FL (US)

(72) Inventor: Steven Michael Hacker, Delray Beach, FL (US)

(73) Assignee: Nano 2.0 Business Press, LLC, Delray Beach, FL (US)

( * ) Notice: Subject to any disclaimer, the term of this patent is extended or adjusted under 35 U.S.C. 154(b) by 192 days.

This patent is subject to a terminal disclaimer.

(21) Appl. No.: 16/236,773

(22) Filed: Dec. 31, 2018

Related U.S. Application Data

(63) Continuation of application No. 14/277,242, filed on May 14, 2014, now Pat. No. 10,166,578.

(60) Provisional application No. 61/862,792, filed on Aug. 6, 2013.

(51) Int. Cl.
| | | |
|---|---|---|
| *B08B 15/04* | (2006.01) | |
| *A61B 46/00* | (2016.01) | |
| *A61B 18/14* | (2006.01) | |
| *B08B 15/00* | (2006.01) | |
| *A61M 1/00* | (2006.01) | |

(52) U.S. Cl.
CPC .............. *B08B 15/04* (2013.01); *A61B 46/00* (2016.02); *A61B 18/1402* (2013.01); *A61B 2218/008* (2013.01); *A61M 1/008* (2013.01); *A61M 2202/02* (2013.01); *B08B 15/00* (2013.01); *B08B 15/007* (2013.01)

(58) Field of Classification Search
CPC ..... B08B 15/04; A61B 46/00; A61B 18/1402; A61B 2218/008
USPC .......................................................... 604/541
See application file for complete search history.

(56) References Cited

U.S. PATENT DOCUMENTS

| | | | | |
|---|---|---|---|---|
| 5,015,243 A | * | 5/1991 | Schifano ................ | A61B 18/00 604/315 |
| 5,288,469 A | * | 2/1994 | Skalla .................... | A61B 18/00 261/DIG. 26 |
| 5,874,052 A | * | 2/1999 | Holland ................. | B01D 46/12 422/122 |
| 5,941,873 A | * | 8/1999 | Korenfeld .......... | A61B 17/0231 604/313 |
| 6,203,590 B1 | * | 3/2001 | Byrd ................... | B01D 46/0023 55/319 |
| 6,663,610 B1 | * | 12/2003 | Thompson ............ | A61M 1/008 604/128 |
| 6,942,650 B1 | * | 9/2005 | Schultz ................. | B01D 46/24 454/66 |
| 2012/0271253 A1 | * | 10/2012 | Schultz ............... | A61M 1/0084 604/319 |

* cited by examiner

*Primary Examiner* — Andrew J Mensh
(74) *Attorney, Agent, or Firm* — Nancy J. Flint, Attorney at Law, P.A.; Nancy J. Flint, Esq.

(57) ABSTRACT

A surgical drape plume evacuator includes a filter enclosure. An operating aperture disposed in the filter enclosure defines an area within the filter enclosure. A pressure source for creating at least one of a negative and positive air pressure in the filter enclosure. A fluid opening in the operating aperture connects the interior of the operating aperture to the interior of the filter enclosure.

14 Claims, 5 Drawing Sheets

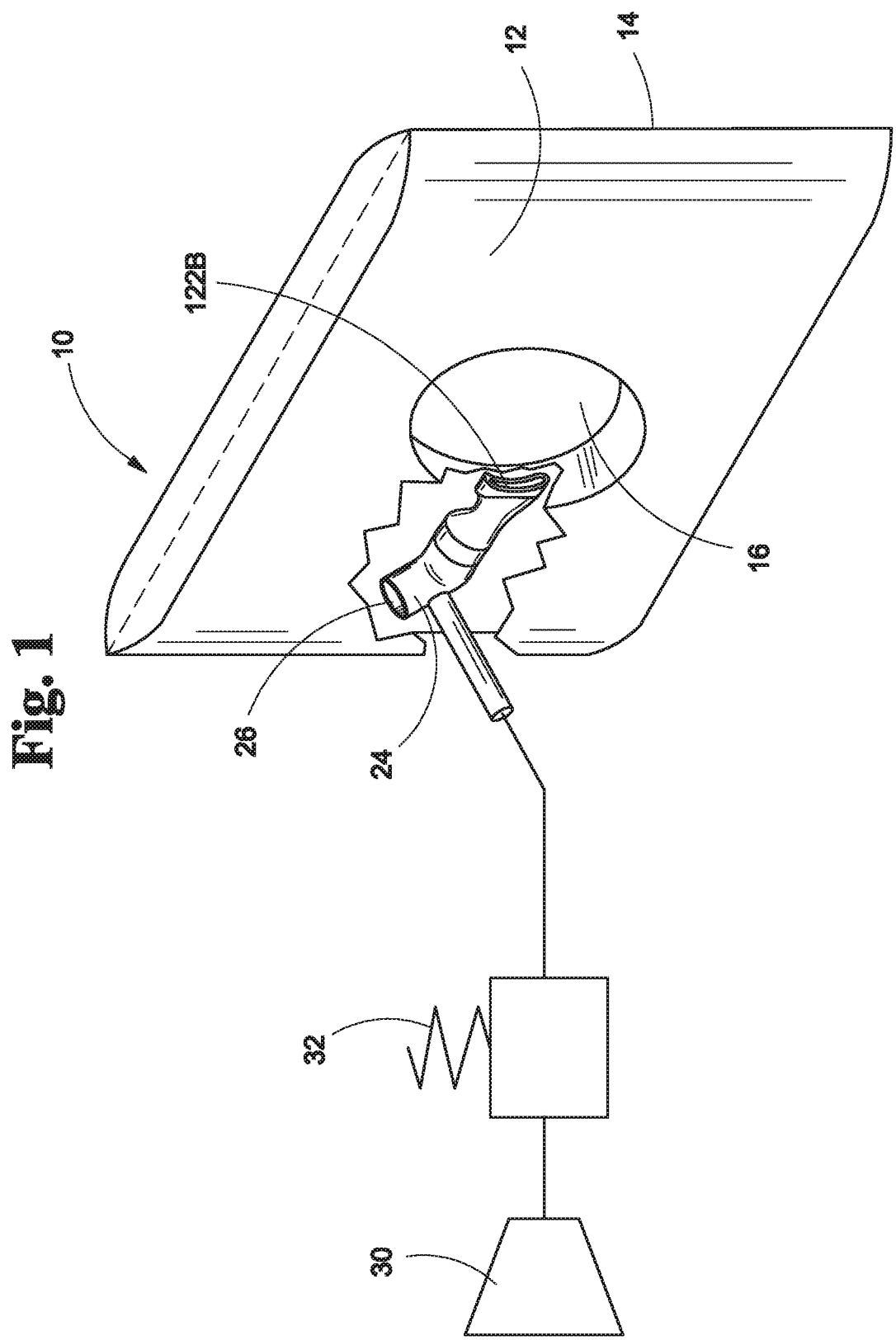

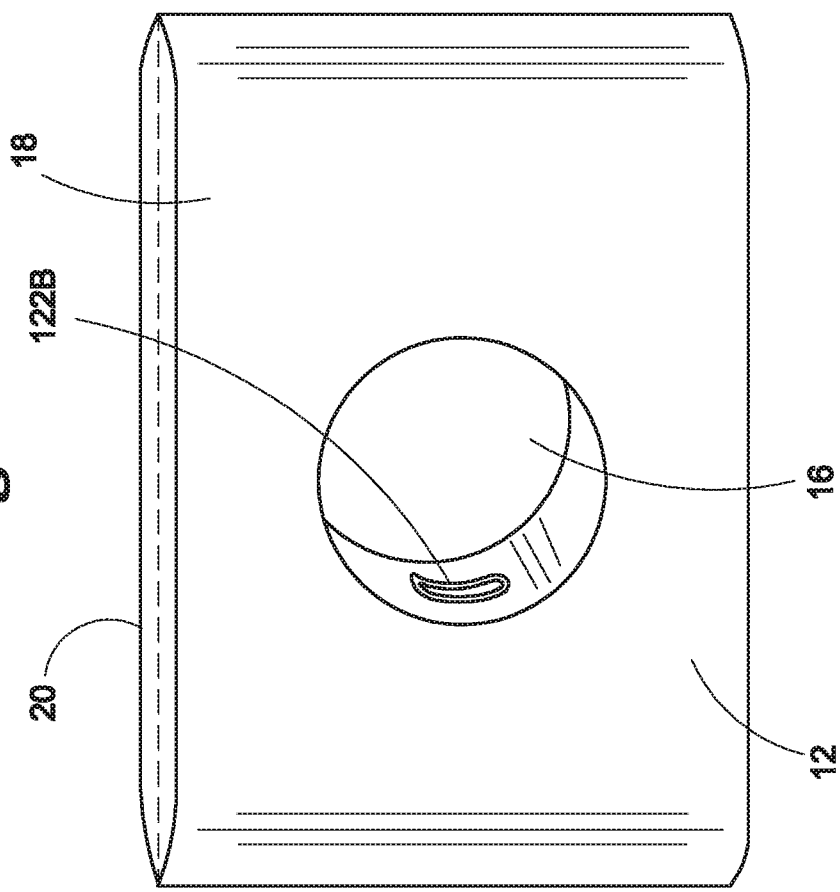

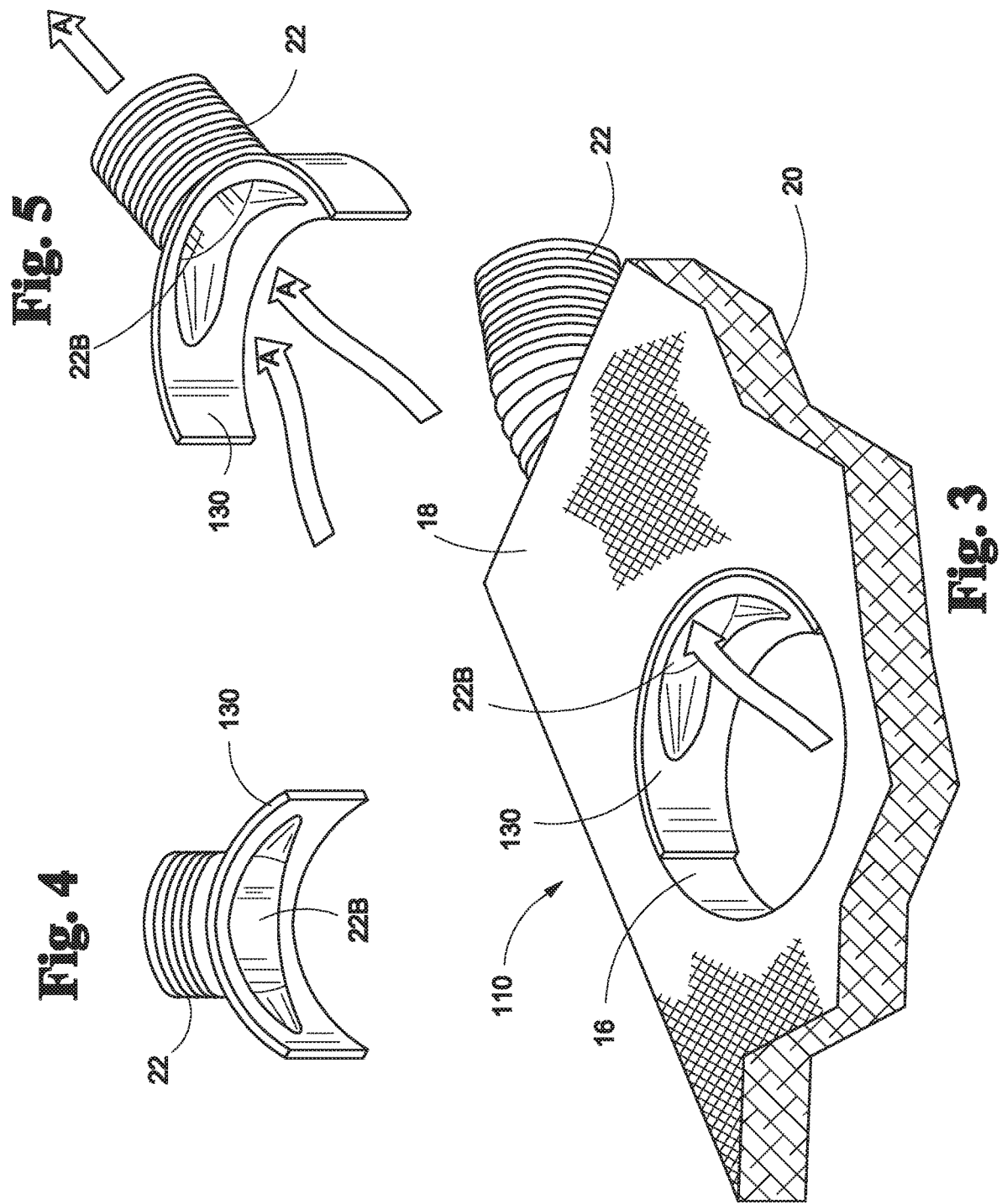

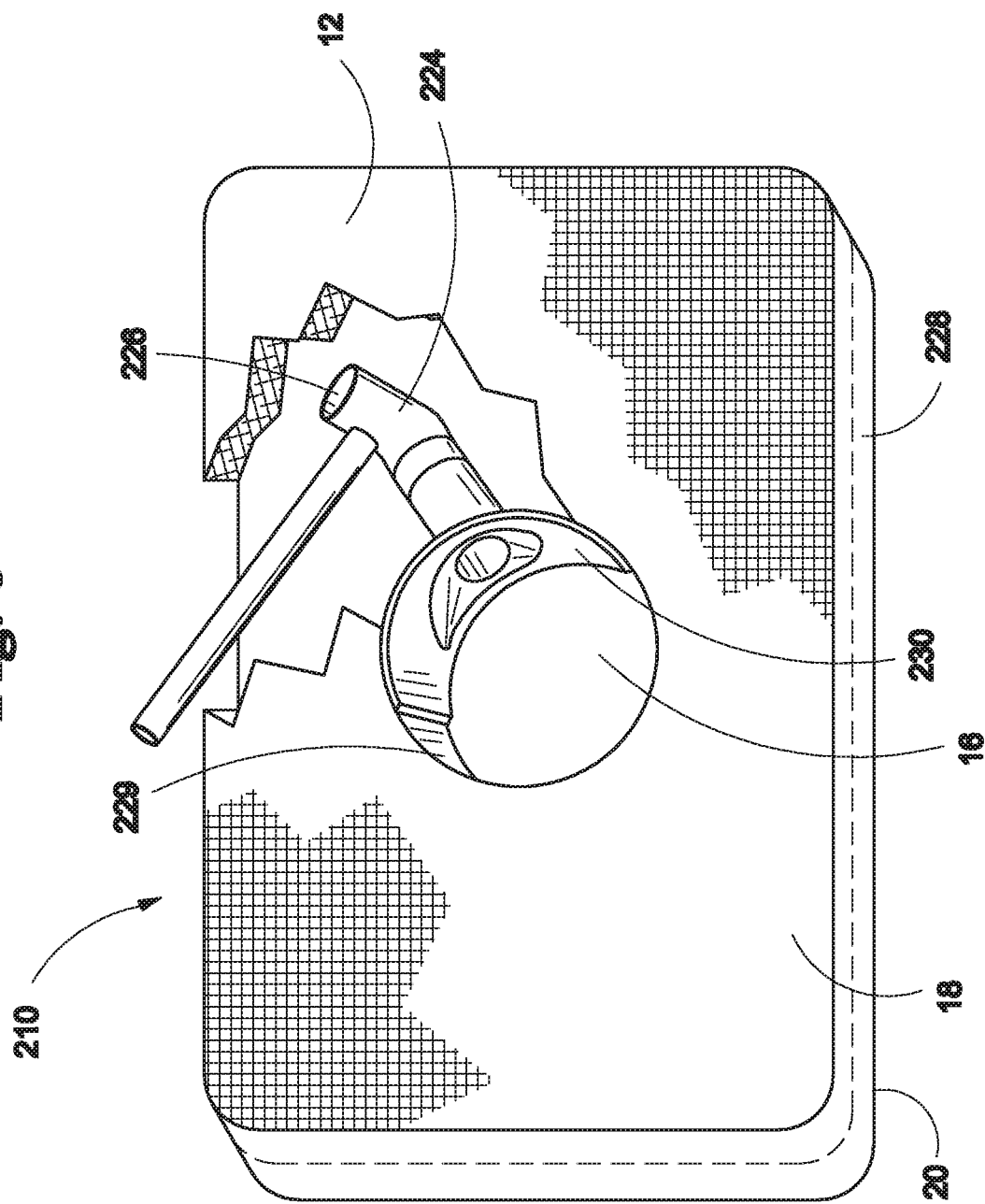

SURGICAL DRAPE PLUME EVACUATOR

BACKGROUND OF THE INVENTION

The present invention relates to improvements in smoke removal in surgical areas, and more particularly to a smoke evacuating device for surgical use, which is simple in structure, can be made of low cost materials, and as a result is disposable.

Handheld electrosurgical instruments are well known in the art. These instruments take the form as electrocautery or laser surgical devices which are used in a multitude of different types of surgeries for the bloodless cutting of tissue with the simultaneous cauterizing of vessels which stop the bleeding. During surgical use, localized heat generated by the electrical discharge or heat source causes noxious smoke to be produced. Because of the high temperatures, the smoke cloud rises rapidly from the point of the incision by the cautery instrument.

Surgical drapes are well known in the art. They are used in minor and major surgeries to keep the operating field sterile and free from contamination. Typically, the surgical drape is fenestrated and has an aperture to enable the surgeon to access the surgical site without contaminating the surgical field. The surgical drape, as it is currently used, has no other function other than to serve as barrier that offers protection from contamination of the surgical field.

Even in the presence of current surgical drapes, the smoke produced during electrosurgery, often has a strong, persistent and unpleasant odor. This noxious odor can cause a vaso-vagal response in conscious patients undergoing minor surgery. Additionally, the smoke comprises organic gases, water vapor, visible and sub-visible solid particles, infectious microbacterial organisms, infectious viruses and virus particles, and carcinogenic substances, each of which is potentially harmful to the patient and the operating room staff. As a result, it is considered good practice to remove the smoke from the surgical field and filter it to minimize any potential harm. Lastly, when produced in sufficient volume, the smoke obscures the surgeon's view of the operative field.

There are prior art systems, making use of a vacuum to remove the smoke, such as that known from U.S. Pat. No. 5,460,602, which places a vacuum nozzle adjacent the cutting tip of the electrocautery device. This device has been satisfactory, however, it suffers from the disadvantage that it requires an entire distinct system which is siamese connected to the existing surgical instrument. This results in a more complex structure, which changes the feel of the surgical instrument, and by adding size to the surgical instrument also may obscure the surgeon's view of the operative field.

Because of this, it is still common practice to have an assistant hold a separate evacuating device near the surgical area. However, this suffers from the disadvantage of requiring two people, who often when not in full coordination, interfere with each other. And, since an additional person is holding the evacuating device in the surgical field, the procedure may require an additional third person to provide surgical assisting such as cutting sutures, retracting tissue and holding instruments in the surgical field. However, too many people can become cumbersome for the surgeon particularly in limited surgical areas. There is also the opportunity cost of requiring additional people for a single operation. Additionally, the use of vacuum devices generating adequate suction is a deterrent to the surgeon as a result of the noise created by the vacuum frequently over 80 db and affecting communication with staff and patient. Lastly, vacuum devices also suffer from power inefficiencies.

It is also known from the art from U.S. Pat. No. 4,921,492 to use a plume evacuator and effector. The plume evacuator includes an evacuation hose adapted for detachable connection to a vacuum generator. There is a filter along the hose. The vacuum head is made of a pliable material to define an evacuation plenum. A porous plenum supporting material is carried within the plenum to provide rigidity to the plenum and to prevent the plenum from collapsing when subjected to the vacuum. This prior art device has also been satisfactory, but it still requires the use of a hose integrally formed with a plenum coupled to expensive noisy and inefficient vacuum equipment. The plenum is integral with a flexible hose which is coupled to a collector head within the plenum formed of a non-porous, pliable synthetic resin. While the pieces are formed of resin, and reusable as the resin may lend itself to a sterilization process, resin pieces are still expensive, and may not be amenable to complete sterilization given the length of the hose necessary to reach a vacuum.

Currently, all prior art systems require the addition of another piece of equipment/device to the surgical field. That device is the sterile surgical drape. All prior art must avoid disturbing the sterile surgical drape and the sterile surgical field or any sterile surgical instrument. The necessity of prior art to avoid contaminating the sterile surgical field and still obviating the need for a surgical drape is often disruptive and burdensome to the surgeon and may be disruptive to the surgery. Prior art necessitates a change by the surgeon to either his instruments, surgical staffs and surgeon's approach to the surgical field, or communication with the patient such that most surgeons choose to not use prior art at great health risk to the surgeon and the patient. Prior art solutions are not readily adopted because it requires these changes and adjustments by the surgeon and the staff.

Accordingly, a plume evacuation system which overcomes the shortcomings of the prior art is desired.

BRIEF SUMMARY OF THE INVENTION

A surgical drape plume evacuator includes a filter enclosure, surgical drape and plume evacuator. An operating aperture is disposed in the filter enclosure and separates an area defined by the operating aperture from the remainder of the filtered enclosure by creating a barrier between the filtered enclosure and the interior of the operating aperture. A pressure source creates at least one of a negative and positive pressure within the filtered enclosure and extending to the operating aperture. The operating aperture provides access to a surgical site and fluidly connects the interior of the operating aperture to the interior of the filtered enclosure.

BRIEF DESCRIPTION OF THE DRAWINGS

Other objects, features and advantages of the present invention will be apparent from the written description and the drawing in which:

FIG. 1 is a schematic plan view of an evacuator constructed in accordance with the invention.

FIG. 2 is a perspective view of the operating aperture portion of the evacuator constructed in accordance with the invention;

FIG. 3 is a perspective view of an evacuator constructed in accordance with a second embodiment of the invention;

FIG. 4 is a front perspective view of a conduit used in the evacuator, constructed in accordance with the invention;

FIG. 5 is a side perspective view of the conduit used in the evacuator constructed in accordance with the invention;

FIG. 6 is a perspective view of an evacuator constructed in accordance with yet another embodiment of the invention;

DETAILED DESCRIPTION OF THE PREFERRED EMBODIMENT

Reference is first made to FIG. 1, in which a surgical drape plume evacuator system, generally indicated as 10, includes a filter enclosure 12 formed of two spaced sheets of porous filter material joined at the edges. Each sheet of the filter material is joined at an edge 14 of enclosure 12, so that if inflated, enclosure 12 takes shape like a pillow. In a preferred embodiment, the filter material is a high efficiency particulate air (HEPA) filter material, to capture 0.3 micron sized matter at 99.7% efficiency or ultra low penetration air (ULPA) filters to capture 0.1 micron sized matter at 99.99% efficiency and include a charcoal filter to remove toxic gases and noxious odors.

Each sheet of enclosure 12 is formed with an operating aperture 16 formed therein. Operating aperture 16 extends through enclosure 12 to provide access for the electrosurgical instrument to the skin upon which the enclosure 12 is placed as discussed in greater detail below. In a preferred embodiment, operating aperture 16 is sufficiently sized to allow for the performance and observation of delicate surgical work, while providing a sufficient space to allow for an incision to accomplish such work. In a preferred embodiment, operating aperture 16 is at least about three inches by three inches, or nine square inches.

Figure 9:
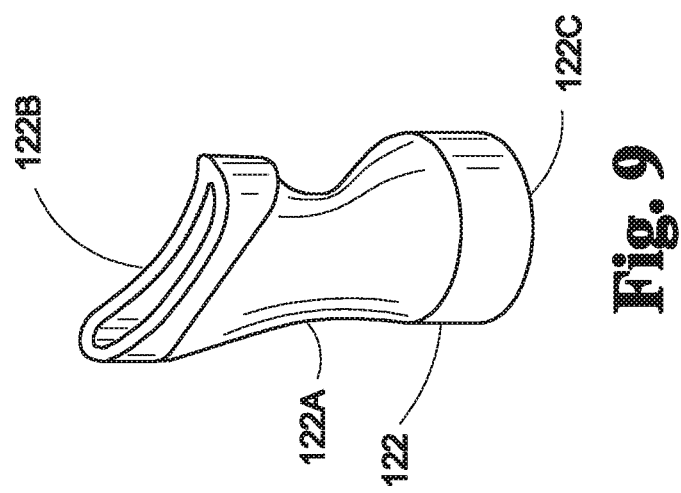
FIG. 9 is a perspective view of the conduit constructed in accordance with the invention.
Figure 8:
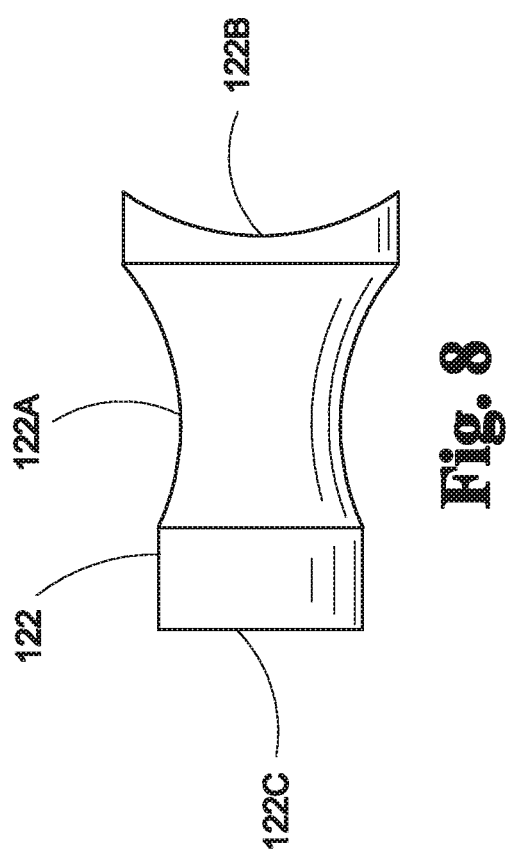
FIG. 8 is a top plan view of the conduit constructed in accordance with the yet another aspect of the invention.
Figure 7:
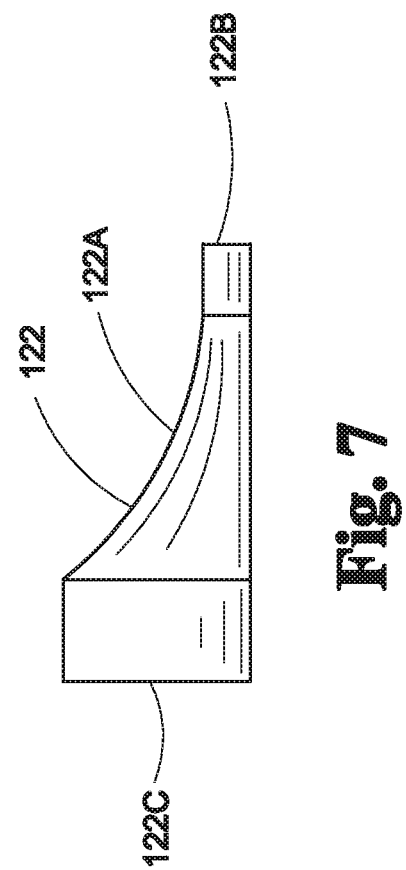
FIG. 7 is a side elevational view of a conduit constructed in accordance with yet another embodiment of the invention.

Reference is now also made to FIG. 2, and FIGS. 7-9. As seen, a conduit 122 is disposed within enclosure 12 between a top sheet 18 and a bottom sheet 20. In a preferred exemplary but non-limiting embodiment, conduit 122 (FIGS. 7-9) is airtight and shaped to flatten and taper along the body 122a from one opening 122c towards the operating aperture 16 and terminating with a mouth (opening) 122b that widens at the aperture itself and is in fluid communication with operating aperture 16. Conduit 122 may be formed as a molded plastic or resin piece.

The air tight conduit 122 is molded to fit at a proximal end 122c in air tight fashion with either one of the sources of positive or negative pressure (i.e., air amplifier 24 or a vacuum hose) and on its distal end is shaped to a widened mouth 122b such that the negative pressure in the operating aperture drags the smoke plume generated through the mouth 122b of the conduit 122. The mouth 122b has a surface area which is widened to cover approximately one fourth to one half the circumference of the operating aperture 16. Additionally, the air tight conduit 122 is shaped so that it forms a circle at its proximal end 122c that it attaches to one of either source of positive or negative pressure (i.e. air amplifier 24 or vacuum hose) and tapers and flattens at its distal end 122b enabling the surgical drape 12 and the conduit 122 to lie flat on the patient's body and not disrupt the surgical field nor disrupt the operating aperture 16.

In one embodiment, a positive pressure source is used to create a negative pressure at the operating aperture. An air amplifier 24 is affixed to the opposed end 122c of conduit 122 and is in fluid communication with conduit 122. Air amplifier 24 has an exhaust 26 which in one embodiment exhausts air within enclosure 12. Because enclosure 12 is made of a filter material, noxious fumes and harmful airborne particles and disease within the plume are drawn from operating aperture 16 and trapped within enclosure 12.

As known in the art, air amplifier 24 (FIG. 1) requires an air pressure source. Accordingly a positive pressure such as an air compressor 30 (FIG. 1) is coupled, optionally through an air regulator 32 (FIG. 1), to be in fluid communication with air amplifier 24. In operation, air compressor 30 forces air into air amplifier 24 which causes a negative air pressure to be formed within conduit 122 and for air to exhaust from conduit 122 through exhaust 26 of air amplifier 24. Because air amplifier 24 is in fluid communication through conduit 122 with operating aperture 16, a negative air pressure is experienced within air operating aperture 16 removing any smoke plume caused by an operation within operating aperture 16 through the mouth opening 122b. The exhausted air fills enclosure 12 and either passes through enclosure 12 as filtered air or remains trapped within enclosure 12. At the end of the operation, air compressor 30 is disconnected from air amplifier 26 and enclosure 12 is thrown away as a hazardous waste material in accordance with protocols known in the art.

The characteristics of air amplifier 24 are chosen to create a vacuum within operating area 16 of between about −6.4 in H2O and −22 in H2O (inches of water column) dead end suction. This vacuum requires compressed air ranging from about 10 psi to 40 psi (pounds per square inch) and air consumption of about 6.8 SCFM to 14.9 SCFM (standard cubic feet per minute). It has been found that a 1% inch amplifier may create enough vacuum though sizes may vary.

It should also be noted, that in a simple embodiment of the invention, rather than separated ply sheets, a single pad may be disposed over conduit 122 to create an enclosing tent over the surgical site enveloped by operating area 16. However, in this embodiment adhesive may be required to affix the enclosure to the skin of the patient. Furthermore, in a preferred embodiment, air amplifier 24 may be affixed within enclosure 12 utilizing an adhesive, a hanging structure formed with a sheet of filter material, a velcro strap or the like. Additionally, that portion of conduit 122 disposed within enclosure 12 may also be affixed in place to a sheet of the enclosure material utilizing velcro, a glue, or other adhesive as known in the art.

In another preferred embodiment, the trigger for turning on and turning off the plume drape evacuator system may be linked to the trigger for turning on and turning off the electrocautery or laser device. In other words, the switch or pedal that controls the electrocautery device may also control air compressor 30. A sensor such as a touchless infrared sensor by way of non-limiting example, may be mounted at either the compressor source or the vacuum source to sense the presence of the use of the electrocautery device or laser and to act as a switch so in this way, the system may be operated in a touchless fashion to start and stop operation coincident with the creation of the smoke plume.

It should be well understood, that compressor 30 provides a positive pressure in the preferred embodiment to activate air amplifier 24 which in turn creates the vacuum at operating aperture 16. An air compressor combined with the use of an air amplifier provides more power efficiency, less noise and is more portable than utilizing a direct vacuum. The addition of the air amplifier within the filter drape enclosure enables a small volume of compressed air to produce a low pressure vacuum effect that is three times the rate of the supplied air. The insertion of the air amplifier in-line within the filter drape provides an air driven, non electric, light with tool, that is quiet, safe, maintenance free and has no moving parts; reducing air consumption by 70 percent and increasing energy efficiency. However, it is well within the scope of the invention to directly couple a vacuum to conduit 122 to create a vacuum within operating aperture 16.

Reference is now particularly made to FIGS. 3-5 in which a drape plume evacuator, generally indicated as 110, constructed in accordance with another embodiment of the invention is provided. For ease of description, like numerals are used to indicate like structure.

In this embodiment, system 110 includes an upper filter layer 18 and a blocking barrier 130 separating upper sheet 18 from lower sheet 20. Blocking barrier 130 prevents diffusion of the smoke plume, i.e., traps it in place. Opening 22b of conduit 22 is disposed in barrier 130 so that air flows in the direction of arrow A from operating aperture 16 into conduit 22. Barrier 130 contains the plume in the vicinity of opening 22b to force more of the plume into conduit 22, away from operating aperture 16 preventing escape.

Another barrier (not shown) at an opposed position about operating aperture 16 may be provided to further contain the smoke plume as it is exhausted through opening 22b.

Reference is now made to FIG. 6 wherein a system 210, constructed in accordance with yet another embodiment of the invention. For ease of description, like numerals are utilized to indicate like structure. System 210 includes filter sheet 18 separated from bottom filter sheet (not shown) by a filter skirt 228 creating the equivalent of a filter pouch. A barrier 230 is formed about operating aperture 16 to encapsulate operating aperture 16 separating operating aperture from the remote of enclosure 12. Barrier 230 is formed of a filter material such as HEPA filter. The filter material may even cover opening 229 which communicates with an exhaust amplifier 224 coupled to an air compressor (not shown) exterior to system 210. In this way, the air is filtered as it passes to amplifier 224 which exhausts the air from exhaust 226 to within the enclosure formed by top sheet 18, bottom sheet 20, side skirt 228 and barrier 230. When done, the entire pouch of system 210 may be disposed. Barrier 230, and barrier 130 may be formed of a sheet of more rigid material; rigid shall mean sufficient rigidity to prevent sheet 18 from collapsing upon sheet 20 during operation.

By providing a surgical drape with an enclosure formed of filtering material about an operating aperture, and placing the operating aperture in fluid communication with a negative pressure source, a system for evacuating the plume of smoke from the use of electrocautery or laser equipment is provided which may be operated by a single person; the surgeon. There is no longer a need to have another person to hold the end of the surgical plume evacuator. Additionally, surgeon and surgical assistants do not need to work around the surgical drape as is necessitated with prior art plume evacuators and thus preventing incidental contamination of the surgical field. There is no longer a need to have extra equipment obscuring the surgical drape aperture and field since the drape itself will provide the function of surgical plume evacuation. Furthermore, by utilizing an air compressor as the pressure source, more power utilizing less electricity, with lower noise, no electricity, and no moving parts, and in the form of a portable device becomes available. This is less annoying for the surgeon and provides a more pleasant experience for the patient. Furthermore, by use of the filtered enclosure, the evacuator may make use of either a positive pressure source or a negative pressure source.

While this invention has been particularly shown and described to reference the preferred embodiments thereof, it would be understood by those skilled in the art that various changes in form and detail may be made therein without departing from the scope of the invention encompassed by the impended claims.

What is claimed as new and desired to be protected by Letters Patent of the United States is:

1. A surgical drape plume evacuator comprising: a filter enclosure comprising two spaced sheets of porous material joined together at the edges of each of the sheets of porous material; an operating aperture disposed in the filter enclosure and defining an area within the filter enclosure, serving as a barrier to keep a surgical field sterile and providing access to a surgical site thereto; a device for providing a negative air pressure to a device that creates the negative air pressure within a conduit that is completely disposed within an interior of the filter enclosure, wherein the conduit is opened at both ends; and a fluid opening in the operating aperture in communication with one open end of the conduit, wherein the conduit connects the operating aperture to the interior of the filter enclosure, wherein the negative pressure created within the conduit by operation of the pressure source and device causes a smoke plume generated during surgery at the surgical site to drag through the conduit and into the interior of the filter enclosure, wherein the smoke plume that is generated during surgery at the surgical site and is dragged through the conduit into the interior of the filter enclosure is completely entrapped within the filter enclosure, wherein none of the smoke plume that is entrapped within the filter enclosure is thereafter released from the interior of the filter enclosure.

2. The surgical drape plume evacuator of claim 1, wherein the device that creates the negative air pressure within the conduit comprises a vacuum.

3. The surgical drape plume evacuator of claim 2, wherein the vacuum is coupled to the conduit via a vacuum hose.

4. The surgical drape plume evacuator of claim 2, wherein the conduit is substantially air tight.

5. The surgical drape plume evacuator of claim 2, wherein the filter material comprises a high efficiency particulate air (HEPA) filter material.

6. The surgical drape plume evacuator of claim 2, wherein the HEPA filter material captures 0.3 micron sized matter or larger at least at 99.7% efficiency.

7. The surgical drape plume evacuator of claim 2, wherein the filter enclosure further comprises a charcoal filter.

8. The surgical drape plume evacuator of claim 2, wherein the filter material captures 0.1 micron sized matter or larger at least at 99.99% efficiency.

9. The surgical drape plume evacuator of claim 8, wherein the filter enclosure further comprises a charcoal filter.

10. The surgical drape plume evacuator of claim 1, further comprising means to turn the pressure source on and off that is linked to a trigger for turning an electrocautery device or a laser on and off.

11. A method for removing a smoke plume within a surgical drape using the surgical drape plume evacuator of claim 2.

12. The method for removing a smoke plume within a surgical drape of claim 11, wherein the smoke plume generated during surgery passes through the filter enclosure.

13. The method for removing a smoke plume within a surgical drape of claim 11, wherein the operation of the surgical drape plume evacuator is coincident with the creation of the smoke plume.

14. The method for removing a smoke plume within a surgical drape of claim 13, wherein the filter enclosure is discarded following surgery.

\* \* \* \* \*